United States Patent [19]
Butler et al.

[11] Patent Number: 5,787,900
[45] Date of Patent: *Aug. 4, 1998

[54] METHOD FOR LOADING AND RELOADING A THERAPEUTICAL DEVICE IN A VASCULARIZED IMPLANTABLE CONTAINMENT APPARATUS

[75] Inventors: Mark D. Butler; Stanley L. Mish, both of Flagstaff, Ariz.

[73] Assignee: Gore Hybrid Technologies, Inc., Flagstaff, Ariz.

[*] Notice: The term of this patent shall not extend beyond the expiration date of Pat. No. 5,626,561.

[21] Appl. No.: 731,353

[22] Filed: Oct. 11, 1996

Related U.S. Application Data

[63] Continuation of Ser. No. 479,932, Jun. 7, 1995, Pat. No. 5,626,561.
[51] Int. Cl.⁶ .................................................. A61B 19/00
[52] U.S. Cl. ........................ 128/898; 604/49; 604/93; 604/890.1
[58] Field of Search ..................... 128/898; 604/49, 604/890.1, 891.1, 19, 52, 93, 21, 27, 28

[56] References Cited

U.S. PATENT DOCUMENTS

| | | | |
|---|---|---|---|
| 4,402,694 | 9/1983 | Ash et al. | 604/891.1 |
| 5,324,518 | 6/1994 | Orth et al. | 424/423 |
| 5,336,237 | 8/1994 | Chin et al. | 606/167 |
| 5,443,508 | 8/1995 | Giampapa | 623/11 |
| 5,626,561 | 5/1997 | Butler et al. | 604/49 |

*Primary Examiner*—Mickey Yu
*Assistant Examiner*—Kelly O'Hara
*Attorney, Agent, or Firm*—Eric J. Sheets

[57] ABSTRACT

This invention relates generally to a method of loading and reloading a therapeutical device in a vascularized implantable containment apparatus made of selectively permeable material. Suitable therapeutical devices for use in the present invention include devices such as drug delivery devices, cell encapsulation devices, or gene therapy devices. A therapeutical device can be easily placed and replaced in a vascularized apparatus of the present invention without damaging tissues associated with the selectively permeable material of the apparatus.

23 Claims, 10 Drawing Sheets

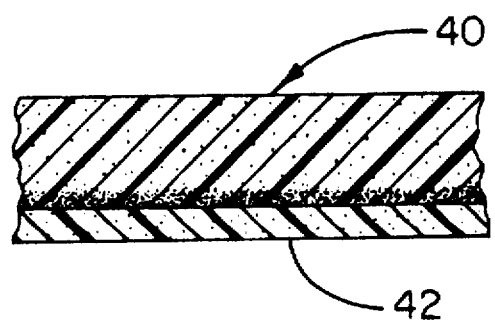
FIG. 4
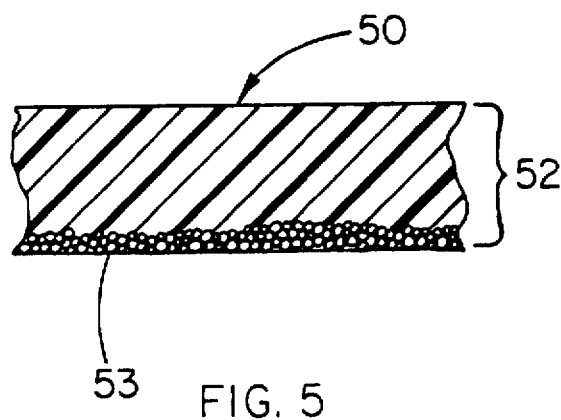
FIG. 5
FIG. 5A
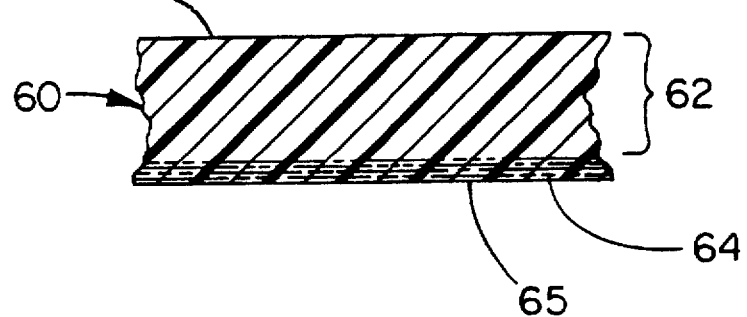
FIG. 6

METHOD FOR LOADING AND RELOADING A THERAPEUTICAL DEVICE IN A VASCULARIZED IMPLANTABLE CONTAINMENT APPARATUS

This application is a continuation of Ser. No. 08/479,932, now U.S. Pat. No. 5,626,561, filed Jun. 7, 1995, and issued Jun. 3, 1997.

FIELD OF THE INVENTION

This invention relates generally to a method of loading and reloading a therapeutical device in a vascularized implantable containment apparatus made of selectively permeable material. Suitable therapeutical devices for use in the present invention include devices such as drug delivery devices, cell encapsulation devices, or gene therapy devices. A therapeutical device can be easily placed and replaced in a vascularized apparatus of the present invention without damaging tissues associated with the selectively permeable material of the apparatus.

BACKGROUND OF THE INVENTION

Various implantable therapeutical devices, such as drug delivery, gene therapy, and cell encapsulation devices, have been disclosed over the years. A common feature of most of these devices is the use of selectively permeable, or semipermeable, membranes to construct all or part of the device. These membranes contain their respective therapeutic agents and delivery systems within the particular device while being permeable to the desired therapeutical product. For cell encapsulation devices, the membranes are also permeable to life sustaining substances and to cellular waste products.

When implanted in a recipient, the typical biological response by the recipient to most of these therapeutical devices is the formation of a fibrotic capsule around the device. With most drug delivery and gene therapy devices, this can limit the performance of the device, particularly when the therapeutic agent has a short half-life. For cell encapsulation devices, a fibrotic capsule encasing the device most often deprives the encapsulated cells of life sustaining exchange of nutrients and waste products with tissues of a recipient. The result is usually fatal to the encapsulated cells. Furthermore, a fibrotic capsule encasing a therapeutical device usually makes surgical retrieval of the device difficult.

When certain therapeutical devices are implanted in a recipient, predominantly vascular tissues of the recipient can be stimulated to grow into direct, or near direct, contact with the device. On one hand, this is desirable because the therapeutical product of the device can then be delivered directly to the circulation of the recipient through the vascular tissues that are in contact with the device. On the other hand, this is undesirable because once vascular tissues of a recipient have grown in contact with one of these implantable therapeutical devices, removal of the device requires surgical dissection of the tissues to expose and remove the device. Surgical dissection of vascular tissues, particularly capillary tissue, can often be a difficult and painful procedure. Whether encased in a fibrotic capsule or surrounded with vascular tissue, the problem of retrieving these implanted devices is a considerable drawback of the devices.

For cell encapsulation devices, an alternative to retrieving and replacing the entire device in a recipient is to retrieve and replace the cells contained in the device. U.S. Pat. No. 5,387,237, issued to Fournier et al., is a representative example of a cell encapsulation device that has at least one opening into the device through which cells can be introduced and removed. Cells are introduced and removed in this, and other similar devices, as a suspension or slurry. Since most cell encapsulation devices are intended to correct a metabolite deficiency in a recipient caused by dysfunction or failure of certain of the recipient's cells, tissues, or organs, the source of the replacement cells is rarely the recipient. In a situation where non-autologous cells are used in this type of cell encapsulation device, the problem of contaminating a recipient with the foreign cells during loading, removal, or refilling of the device is ever present. One solution to this contamination problem would be to enclose the cells in a container that can be placed, removed, and replaced in a device as a unit.

A retrievable cell encapsulation envelope enclosed in an implantable permselective membrane for use as an artificial endocrine gland is disclosed in U.S. Pat. No. 4,378,016 issued to Loeb. The Loeb device comprises a housing made of an impermeable hollow stem and a permselective membrane sack. The hollow stem has a distal end defining an extracorporeal segment, a percutaneous segment in the mid-region, and a proximal end defining a subcutaneous segment. The sack is adapted to receive an envelope containing hormone-producing cells and has an access opening that is coupled to the proximal end of the hollow stem. In a preferred embodiment, the cell containing envelope is in the form of a flexible collar. The flexible collar is partially collapsible to allow for easier placement and replacement of the envelope in the sack. Once in place, the flexible collar also provides a snug fit between the envelope and the sack. Placement and replacement of a cell containing envelope in the sack portion is accomplished manually with forceps, or the like. Retrieval of the envelope from the sack can be aided with a guidewire attached to the envelope. In one embodiment of the Loeb device, the sack has openings at both ends that are implanted percutaneously. In this embodiment, the cell containing envelope may be inserted or removed through either end of the device.

The housing of the Loeb device is surgically implanted in a recipient through the abdominal wall so the distal end of the stem protrudes from the recipient, the proximal end of the stem resides subcutaneously with respect to the abdominal wall, and the sack portion is placed in the peritoneal cavity surrounded in peritoneal fluid. According to Loeb, the sack allows hormones, nutrients, oxygen, and waste products to flow in and out of the sack while preventing bacteria from entering the patient. The sack and the envelope are said by Loeb to be permeable to nutrients and hormones, but impermeable to the hormone-producing cells and immune response bodies. Upon implantation of the device in a patient, the cells contained therein are said to take over the function of the corresponding natural gland, sense the amount of hormone needed, and produce the correct amount of the desired hormone.

Implanted cell encapsulation devices, particularly those intended as an artificial endocrine gland, usually require a high rate of flux of nutrients and waste products between the encapsulated cells in the device and tissues of the recipient. Having a cell encapsulation device in close, or direct, association with a vascular structure usually provides the highest rate of nutrient and waste product flux for such a device. Loeb does not teach the value of vascularization of the sack portion of the housing, however. Nor is the Loeb device implanted in a part of the body that is particularly vascularized.

Brauker et al. disclose a cell encapsulation device in U.S. Pat. No. 5,314,471 that requires close association of host vascular structures with the device. According to Brauker et al., "conventional implant assemblies and methodologies usually fail to keep the implanted cells alive long enough to provide the intended therapeutic benefit." Cell death in these implanted devices is said by Brauker et al. to be due in large part to an ischemia imposed on the cells during the first two weeks following implantation. Brauker et al. conclude that "the cells die because conventional implant assemblies and methodologies themselves lack the innate capacity to support the implanted cells' ongoing life processes during the critical ischemic period, when the host's vascular structures are not nearby." Brauker et al. state that in order for implanted cells to survive and function on a long term basis, the host must grow new vascular structures in association with the device. Brauker et al. note that a host will not naturally provide new vascular structures to an implanted cell encapsulation device. According to Brauker et al., the host must be stimulated by the implant assembly itself to grow new vascular structures close to the cell encapsulation device. Angiogenic stimulus can be provided by angiogenic factors applied to the cell boundary of the Brauker et al. device or by certain cell types encapsulated in the device. Growth of vascular tissue in association with a device of Brauker et al. will make removal of the device from a host difficult, however.

An implantable containment apparatus made of selectively permeable polymeric material that permits a therapeutical device, such as a drug delivery, a gene therapy, or a cell encapsulation device, to be placed and replaced in a recipient without damaging or disturbing tissues associated with the selectively permeable polymeric material would be useful. Such an apparatus that becomes closely associated with vascular structures without the need to supply angiogenic factors to induce the close vascularization would also be useful. A method of easily placing and replacing a therapeutical device in an implantable containment apparatus of the present invention would be further useful.

SUMMARY OF THE INVENTION

The present invention is directed to an implantable containment apparatus for a therapeutical device, such as a drug delivery device, a cell encapsulation device, or a gene therapy device. The apparatus is primarily made of selectively permeable material. The selectively permeable material permits flux, or exchange, of solutes between a therapeutical device contained in the apparatus and tissues of a recipient, while excluding cells from growing beyond a desired point through the material. When an apparatus is implanted in a recipient, various tissues from the recipient grow to associate with the apparatus. These tissues grow next to, or partially through, the exterior surface of the apparatus. It is preferred that vascular tissue is the predominant tissue that grows to associate with an apparatus of the present invention. Once growth of a recipient's tissues in association with an apparatus of the present invention has occurred, a therapeutical device can then be easily placed and replaced in the apparatus without damaging or disturbing the tissues associated with the selectively permeable material of the apparatus.

This is preferably accomplished by providing an implantable containment apparatus for a therapeutical device comprising a selectively permeable microporous polymeric material in the form of a tube wherein the tube comprises an exterior surface, an interior surface that defines a luminal space of substantially uniform diameter, and an access means at one end of the tube through which a therapeutical device is insertable into the luminal space of the tube wherein, once a therapeutical device is inserted into the luminal space of the tube, the therapeutical device is retained within the tube wherein biochemical and therapeutic substances having a molecular weight up to about 5,000,000 MW diffuse across the thickness of the tube between the contents of the therapeutical device contained therein and tissues of a recipient wherein the therapeutical device is removable from the tube through the access means of the tube and wherein the tube is refillable with a therapeutical device through the access means of the tube. The apparatus can also have an access means at each end of the tube. In this embodiment, a therapeutical device can be inserted and removed from the luminal space of the tube through either access means in the tube. Furthermore, in this embodiment, a fluid stream can be established through both access means of the tube that can then be used to flush a therapeutical device in and out of the luminal space of the tube.

Accordingly, the present invention is also directed to a method in which a therapeutical device, such as a drug delivery device, a gene therapy device, or a cell encapsulation device, is easily inserted into, removed from, and replaced in a containment apparatus of the present invention as a unit with a fluid stream. The method involves repeatedly filling and emptying an implantable containment apparatus tube with a therapeutical device, which comprises:

(a) providing an implantable containment apparatus in the form of a tube comprised of a selectively permeable polymeric material having an exterior surface, an interior surface defining a luminal space of substantially uniform diameter, and an access means at each end of the tube that permits access to the luminal space of the tube;

(b) opening both access means of the implantable containment apparatus tube to access the luminal space of the tube;

(c) providing a means of establishing and maintaining a fluid stream through the luminal space of the implantable containment apparatus tube;

(d) connecting the fluid stream means of step (c) to one of the opened access means of the implantable containment apparatus tube;

(e) establishing a fluid stream through the luminal space of the implantable containment apparatus tube with the fluid stream means of step (c);

(f) entraining a therapeutical device in the fluid stream;

(g) delivering the entrained therapeutical device into the luminal space of the implantable containment apparatus with the fluid stream;

(h) discontinuing the fluid stream;

(i) disconnecting the fluid stream means of step (c) from the opened access means;

(j) closing both access means of the implantable containment apparatus to contain the therapeutical device within the luminal space of the implantable containment apparatus;

(k) providing a means of establishing and maintaining a fluid stream around the therapeutical device and through the luminal space of the implantable containment apparatus;

(l) opening both access means of the implantable containment apparatus;

(m) connecting the fluid stream means of step (k) to one of the opened access means of the implantable containment apparatus;

(n) establishing a fluid stream around the therapeutical device and through the luminal space of the implantable containment apparatus tube to entrain the therapeutical device in the fluid stream;

(o) removing the entrained therapeutical device from the luminal space of the implantable containment apparatus with the fluid stream of step (n); and (p) repeating steps (c) through (o) as desired.

Other features and advantages of the invention will become apparent upon review of the following specification, drawings, and claims.

BRIEF DESCRIPTION OF THE DRAWINGS

FIG. 4 illustrates a cross-section of a microporous polymeric material of the present invention (40) wherein the selective permeability of the material is varied sharply across the thickness of the material with an additional layer of microporous polymeric material (42).

FIG. 5 illustrates a cross-section of a microporous polymeric material of the present invention (50) wherein the selective permeability of the material (52) is varied sharply across the thickness of the material with a hydrogel material (53).

FIG. 5A illustrates a cross-section of a microporous polymeric material of the present invention (51) wherein the selective permeability of the material (52) is varied sharply across the thickness of the material with an additional layer of microporous polymeric material (55) and a further layer of hydrogel material (54).

FIG. 6 illustrates a cross-section of a microporous polymeric material of the present invention (60) having a cell permeable zone (62) beginning at the exterior surface (63) of the material and continuing across the thickness of the material to a cell exclusion zone (64) within the material adjacent to and continuous with the interior surface (65) of the material.

FIG. 15C also includes an illustration of two fluid stream means (155 and 156) and a connector (157), having a cavity with a pin (158) on one side (hereinafter the "pin-side") and a cavity (159) on the other side of the connector (157) without a pin (hereinafter the "non-pin-side"), that is adapted to mate with the access means (152) of the apparatus (150) to facilitate placement, retrieval, or replacement of a therapeutical device in the apparatus.

Figure 1:
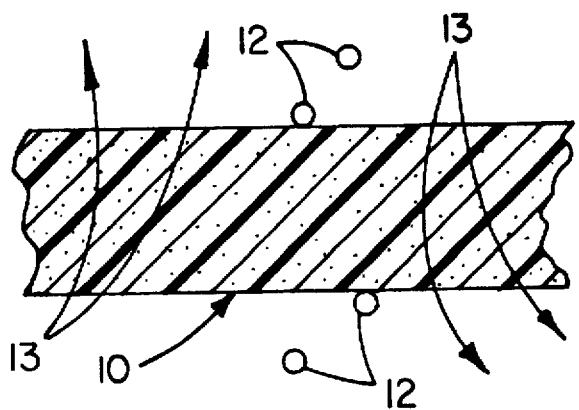
FIG. 1 illustrates a cross-section of a microporous polymeric material of the present invention (10) wherein the selective permeability of the material excludes cells (12) from migrating or growing into the porous spaces of material while permitting bi-directional flux of solutes (13) across the thickness of the material.

It is understood that the inventions are not limited in use to the details of construction or methodologies there set forth or as illustrated in the drawings. The invention is capable of other embodiments and of being practiced and carried out in various ways.

DETAILED DESCRIPTION OF THE INVENTION

The present invention is directed to an implantable apparatus for containment of a therapeutical device, such as a cell encapsulation device, a drug delivery device, or a gene therapy device. Once positioned within the apparatus, the permeable portion of the exterior surface of the therapeutical device and the inner, or luminal, surface of the apparatus are preferably in direct contact. When containing a therapeutical device, an implanted apparatus permits exchange of biochemical substances and therapeutic agents across the thickness of the tube between the contents of the device and tissues of a recipient. An important feature of the present invention is the ability to easily place and replace such a device in an implanted apparatus without damaging tissues of a recipient associated with the apparatus.

The apparatus of the present invention is made in a shape that conforms, at least in part, to the form of the therapeutical device the apparatus is intended to contain. With cylindrical therapeutical devices, for example, an apparatus of the present invention is preferably in a tubular form. Other shapes contemplated for the present invention include, but are not limited to, discs, spheres, inflated ovals, cylinders, and/or irregular geometric shapes.

The present invention is made, primarily, of a porous polymeric material having selective seiving properties. A selectively seiving porous polymeric material controls passage of solutes, biochemical substances, viruses, and cells, for example, through the material, primarily on the basis of size. In general, as the average pore size of a porous polymeric material increases, increasingly larger biochemicals and biological entities are able to pass through the material. In the present invention selectively seiving porous polymeric materials capable of preventing the passage of biological cells through the material, while permitting biological molecules to pass through the material, are preferred.

Porous polymeric materials suitable for construction of an apparatus of the present invention include, but are not limited to, stretched polytetrafluoroethylene, stretched polypropylene, stretched polyethylene, or porous polyvinylidene fluoride, woven or non-woven collections of fibers or yarns, such as "Angel Hair," described by W. French Anderson in Science, vol. 246, pp747–749, or by Thompson et al. in Proc. Natl. Acad. Sci. USA, vol. 86, pp7928–7932 (1989), or fibrous matrices, such as those described by Fournier, et al. in U.S. Pat. No. 5,387,237, either alone or in combination. Stretched, or expanded, polytetrafluoroethylene is preferred. Stretched polytetrafluoroethylene is characterized as a porous material having void spaces defined by nodes and fibrils. Methods for making stretched polytetrafluoroethylene are taught by Gore in U.S. Pat. Nos. 3,953,566 and 4,187,390, each of which is incorporated herein by reference.

For stretched polytetrafluoroethylene, or similar fibrillated material, the pore size is related to the fibril length of the material and the thickness of the material. Pore size may be measured by porometry, such as that provided by the Coulter porometer (Coulter Corp.) Alternatively, fibril length is measured as described in U.S. Pat. No. 4,482,516, issued to Gore, which is incorporated herein by reference.

The fibril length of porous stretched polytetrafluoroethylene that has been stretched, or expanded, in a single direction is defined herein as the average of ten measurements between nodes connected by fibrils in the direction of stretching. Ten measurements are made in the following manner. First, a photomicrograph is made of a representative portion of the sample surface, of adequate magnification to show at least five sequential fibrils within the length of the photomicrograph. Two parallel lines are drawn across the length of the photomicrograph so as to divide the photograph into three equal areas, with the lines being drawn in the direction of stretching and parallel to the direction of orientation of the fibrils. Measuring from left to right, five measurements of fibril length are made along the top line in the photograph beginning with the first node to intersect the line near the left edge of the photograph and continuing with consecutive nodes intersecting the line. Five more measurements are made along the other line from right to left beginning with the first node to intersect the line on the right hand side of the photograph. The ten measurements obtained by this method are averaged to obtain the fibril length of the material.

For a porous stretched polytetrafluoroethylene material that has been stretched in more than one direction, the fibril length is estimated by examining a representative photomicrograph of the material surface and comparing fibril lengths as described above in a manner that represents the various directional orientations of the fibrils.

Thicker fibrillated materials generally have more tortuous pathways connecting one end of a pore to the other end of the pore. As a result, a thicker fibrillated material may have pores that are larger than the entity sought to be excluded by the pores, but will remain resistant to passage of the entity through the pores due to the increased tortuosity of the pathways of the pores in the thicker material. In the present invention, the fibril length and the thickness of a stretched polytetrafluoroethylene material is chosen to form pores that resist cellular ingrowth across the thickness of the material beyond a desired point, while being selectively permeable to macromolecules up to a molecular weight of about 5,000,000 MW.

For some selectively permeable porous polymeric materials suitable for use in the present invention, the molecular weight cutoff, or sieving property, of the material begins at the surfaces of the material. As a result, certain solutes and/or cells do not enter and pass through the porous spaces of the material from one side to the other. This does not prevent cells from growing next to or on the exterior surface of the material, however. (See FIG. 1) In one embodiment, tissues of a recipient, including vascular endothelial cells, grow to contact, but not penetrate, the exterior surface of the present invention. The vascular endothelial cells can combine to form capillaries thereon. Such capillary formation or neovascularization of the present invention permits fluid and solute flux between tissues of a recipient and the contents of a therapeutical device to be enhanced.

Figure 2:
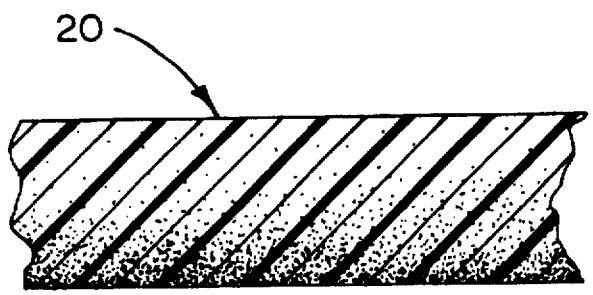
FIG. 2 illustrates a cross-section of a microporous polymeric material of the present invention (20) wherein the selective permeability of the material varies continuously across the thickness of the material as indicated by the gradually increasing density of the stippling in the figure.
Figure 3:
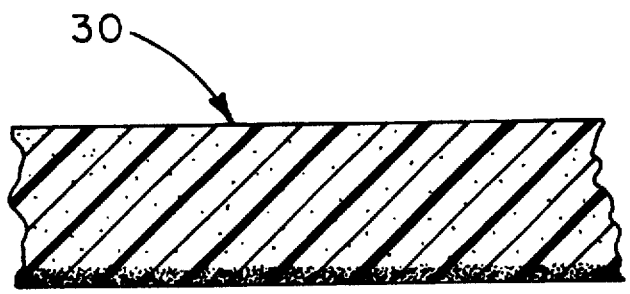
FIG. 3 illustrates a cross-section of a microporous polymeric material of the present invention (30) wherein the selective permeability of the material varies sharply across the thickness of the material as indicated by the sharply increasing density of the stippling in the figure.

Other selectively permeable porous polymeric materials can be constructed or modified to have a selective permeability that varies across the thickness of the material. The permeability of a porous polymeric material can be varied continuously across the thickness of the material (See FIG. 2) or varied sharply from one cross-sectional area of the material to another to form a stratified structure. (See FIG. 3)

In one embodiment of the present invention, the permeability of a porous polymeric material is varied across its thickness with additional layers of porous polymeric material. (See FIG. 4) The additional layers of porous polymeric material may have the same composition and permeability as the initial layer of material or the additional layers may be of a different composition and/or permeability.

In another embodiment, the selective permeability of a porous polymeric material for use in the present invention is varied by impregnating the void spaces of the porous polymeric material with a hydrogel material. Hydrogel material can be impregnated in substantially all of the void spaces of a porous polymeric material or in only a portion of the void spaces. For example, by impregnating a porous polymeric material with a hydrogel material in a continuous band within the material adjacent to and/or along the interior surface of a porous polymeric material, the selective permeability of the material is varied sharply from an outer cross-sectional area of the material to an inner cross-sectional area of the material. (See FIG. 5) The amount and composition of hydrogel material impregnated in a porous polymeric material depends in large part on the particular porous polymeric material used to construct an apparatus of the present invention, the degree of permeability required for a given application, and the biocompatibility of the hydrogel material. Examples of suitable hydrogel materials for use in the present invention include, but are not limited to, HYPAN® Structural Hydrogel (Hymedix International, Inc., Dayton, N.J.), non-fibrogenic alginate, as taught by Dorian in PCT/US93/05461, which is incorporated herein by reference, agarose, alginic acid, carrageenan, collagen, gelatin, polyvinyl alcohol, poly(2-hydroxyethyl methacrylate, poly(N-vinyl-2-pyrrolidone), or gellan gum, either alone or in combination. HYPAN® Structural Hydrogel is preferred. The total thickness of a stretched polytetrafluoroethylene/hydrogel composite ranges from about 2 microns to about 1000 microns.

The permeability of the porous polymeric material can be varied sharply across the thickness of the material with an additional layer of porous polymeric material and a further layer of hydrogel material. (See FIG. 5A) An advantage of this embodiment is the additional protection provided an implant recipient against contamination with cells from a failed cell encapsulation device contained in an apparatus of the present invention. In addition, this configuration will provide a strong cell and humoral immunoisolation barrier.

In one embodiment, the permeability of the porous polymeric material is selected to permit growth of cells from a recipient into, but not through, the material. In this embodiment, a cell permeable zone is formed in the void spaces of a porous polymeric material starting at the exterior surface of the material and continuing to a point within the material adjacent to the interior surface of the apparatus where the permeability of the porous polymeric material to cells is sharply decreased so that cells that have migrated into the void spaces of the material cannot migrate further and penetrate the interior surface of the apparatus (See FIG. 6). These properties of the present invention are referred to herein as being impervious to cellular ingrowth. The region of the porous polymeric material in which cells cannot migrate or grow is referred to as a cell exclusion zone. A cell exclusion zone in an apparatus of the present invention prevents invasive cells from entering the lumen of the apparatus and contacting, adhering to, fouling, ingrowing, overgrowing, or otherwise interfering with a therapeutical device contained within the apparatus. To exclude invading host cells from growing through to the interior surface of the apparatus, the pore size of the cell exclusion zone should be less than about 5 microns, preferably less than about 1 micron, most preferably less than about 0.5 microns, as measured by porometry, or the permeability suitably adjusted with a hydrogel material.

Figure 10:
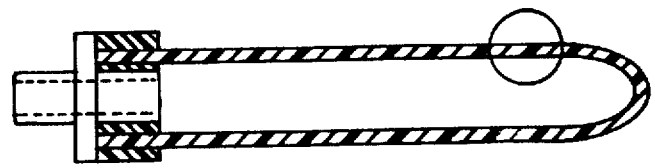
FIG. 10 illustrates the embodiment depicted in FIG. 9A, but with a cell exclusion zone formed with a hydrogel material instead of a layer of a microporous polymeric material.
Figure 10A:
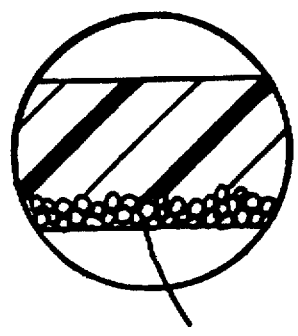
FIG. 10A is an enlargement of the circled area of FIG. 10 illustrating a cell exclusion zone formed with hydrogel material (103) instead of a layer of a microporous polymeric material as depicted in FIG. 9A.

A cell exclusion zone can be formed in a stretched polytetrafluoroethylene material having a cell permeable zone by impregnating the void spaces of the polytetrafluoroethylene material with a hydrogel material in a continuous band within the polytetrafluoroethylene material adjacent to and/or along the interior surface of the stretched polytetrafluoroethylene material of an apparatus. (See FIG. 10) The preferred hydrogel material is a HYPAN® Structural Hydrogel (Hymedix International Inc., Dayton, N.J.) In particular, gel (Hymedix International Inc., Dayton, N.J.) In particular, HYPAN® Structural Hydrogel catalog numbers HN-68 and/or HN-86 are suitable for use in the present invention. In general, the hydrogel material comprising the cell exclusion zone has a thickness ranging from about 2 microns to about 100 microns, preferably between about 25 microns and about 50 microns. In general, a hydrogel material used to form a cell exclusion zone in a stretched polytetrafluoroethylene material of the present invention is impregnated into the void spaces of the polytetrafluoroethylene materials after the material has been shaped substantially into its final form. A hydrogel material is rarely subjected to the temperatures described below for laminating stretched polytetrafluoroethylene materials together.

Various cell types can grow into the cell permeable zone of a porous polymeric material of an apparatus of the present invention. The predominant cell type that grows into a particular porous polymeric material depends primarily on the implantation site, the composition and permeability of the material, and any biological factors, such as cytokines and/or cell adhesion molecules, for example, that may be incorporated in the material or introduced through the apparatus. Suitable biological factors for use in the present invention include, but are not limited to, protein and peptide cytokines, such as vascular endothelial growth factor (VEGF), platelet derived endothelial cell growth factor (PD-ECGF), fibroblast growth factor (FGF), peptides with the amino acid sequence gly-his-lys or their palindromes, with or without salt-bridged copper (II), polysaccharides with angiogenic activity, such as heparin, angiogenesis stimulating lipids, such as oleic acid, or metals, such as copper, either alone or in combination.

Figure 7:
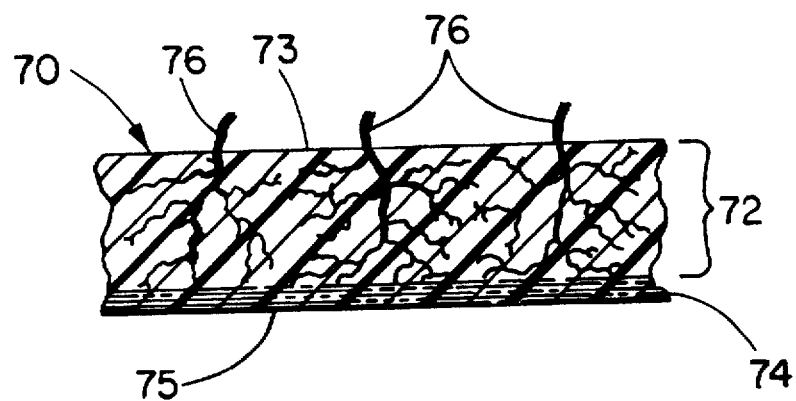
FIG. 7 illustrates a cross-section of a microporous polymeric material of the present invention (70) having a cell permeable zone (72) beginning at the exterior surface (73) of the material and continuing across the thickness of the material to a cell exclusion zone (74) within the material adjacent to and continuous with the interior surface (75) of the material, wherein the cell permeable zone (72) is populated with vascular structures (76).

In the preferred embodiment, vascular endothelium is the predominant cell type that grows into a porous polymeric material for use in the present invention. Vascularization of the porous polymeric material by a well established population of vascular endothelial cells in the form of a capillary network is encouraged to occur as a result of neovascularization of the material from tissues of a recipient into and across the thickness of the material very close to the interior surface of the apparatus, but not across the cell exclusion zone. (See FIG. 7) Though vascularization of the present invention can occur without the addition of biological factors, angiogenic factors, such as those mentioned above, can be used to enhance vascularization of the apparatus. In addition, angiogenesis can be stimulated by conditions, such as hypoxia. This neovascularization of an apparatus of the present invention improves mass transport of therapeutic drugs or biochemical substances between the interior surface of the apparatus and tissues of a recipient, thereby enhancing the quantity and rate of transport of therapeutic drugs or biochemical substances between the contents of a therapeutical device contained in the apparatus and tissues of the recipient. In higher animals, nearly all cells are within about 100 microns of a capillary. Therefore, to achieve maximum exchange of materials between a therapeutical device and tissues of a recipient, it is preferred that the maximum distance ingrown capillaries should be from the lumen of the present invention is less than about 100 microns, more preferably less than about 50 microns, and most preferably less than about 25 microns. Accordingly, the cell exclusion zone in this embodiment of the apparatus should be less than about 100 microns, preferably less than about 50 microns, and most preferably less than about 25 microns, in thickness. In addition to permitting vascularization of the porous polymeric material, the permeability of the porous polymeric material is chosen to selectively permit passage of biochemical substances, including therapeutic drugs, having molecular weights up to about 5,000,000 MW across the thickness of the material. Since a chronic inflammatory response to the present invention has not been observed in experimental animals, it is believed that vascularization of the apparatus proceeds along with the wound healing process of the implantation site.

Vascularization and other tissue ingrowth of the cell permeable zone of an apparatus of the present invention anchors the apparatus in the implantation site. This is an important feature, as migration of conventionally implanted therapeutical devices is often a concern. For a tubular apparatus of the present invention, anchorage of the apparatus in an implantation site with ingrown host tissues assists in maintaining the shape of the implanted apparatus. Maintaining the shape of a tubular apparatus of the present invention is often necessary for easy placement, replacement, and proper functioning of a therapeutical device contained in the apparatus.

It is speculated that vascularization of a porous polymeric material of the present invention could also be accomplished by culturing a population of autologous, or immunogenically neutralized, vascular endothelial cells on the exterior surface of an apparatus that would grow and assemble into capillaries connected to the recipient's circulatory system. A vascular subendothelial matrix substrate, such as collagen, fibronectin, laminin, or derivatives thereof, applied to the exterior surface of the porous polymeric material followed by seeding the substrate with cells should allow the cells to grow and differentiate into capillaries thereon. A commercially available subendothelial cell matrix that may be suitable for this purpose in experimental rats is a preparation known under the tradename Matrigel. (Collaborative Laboratories, Inc.) Alternatively, a suitable subendothelial matrix preparation may be obtainable from the vasculature of the implant recipient.

Figure 8:
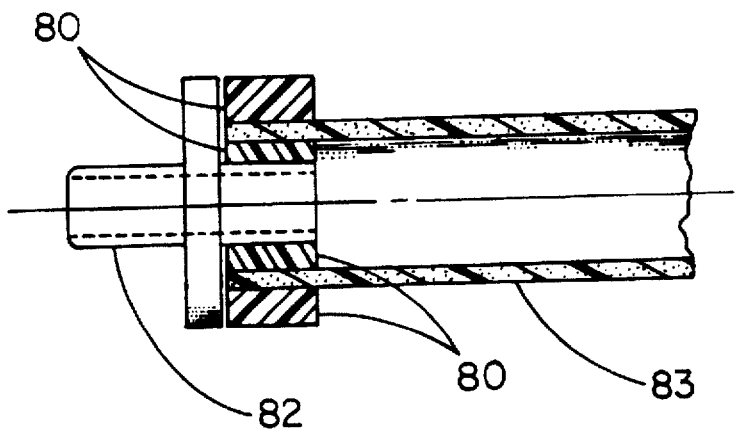
FIG. 8 is a cross-sectional illustration of a tubular embodiment of the present invention wherein an adhesive (81) is used to attach an access means (82) to a microporous polymeric material (83).

An apparatus of the present invention has one or more access means through which a therapeutical device is placed, retrieved, and replaced in the apparatus. An access means is a closeable opening. The closeable opening is preferably a resealable port, or housing, secured through the porous polymeric material of an apparatus of the present invention or secured in an open end of a tubular, or similarly shaped, apparatus configuration. An access means can have any shape suitable for facilitating placement, retrieval, and replacement of a therapeutical device in the luminal space of a particular apparatus embodiment. Commercially available fittings, such as Luer-lok connectors (Value Plastics, Inc., Fort Collins, Colo.), can also be used as an access means in the present invention. In one method, an access means is attached to the porous polymeric material of the present invention with a strong, biocompatible adhesive, such as the thermoplastic fluorinated ethylene propylene. (FEP) In a tubular embodiment of the present invention, for example, a preferred access means is a hollow cylindrically shaped fitting made of full density polytetrafluoroethylene (TEFLON®) having a first portion that fits snugly inside an end of the tube component of the present invention and a second portion that extends beyond the end of the tube component to receive and retain a sealing means. The access means is attached to the tube component by wrapping the first portion of the fitting with an FEP film to a thickness of about 30–40 microns. The FEP film is heat-shrunk in place with hot air. The open end of the tube is stretched slightly as the FEP-wrapped first portion of the access means is inserted into the end of the tube. Heat is applied to the access means in the area of the FEP between the access means and tubular component to a temperature in excess of that required to melt and shrink the FEP material, about 285° C., but not high enough to damage the polytetrafluoroethylene material of the tubular component or the access means. Melting the FEP material wrapped around the first portion of the access means causes the FEP to flow into the pores of the stretched polytetrafluoroethylene material and over the surface of the first portion of the access means. Upon cooling, the FEP tenaciously adheres these components together. Optionally, a piece of FEP shrink-wrap film is wrapped around the exterior surface of the tubular component above the underlying first portion of the access means. (See FIG. 8) Upon heating and cooling, the FEP will contract. The contracted FEP will function as a compression ring on the tubular component and the access means of the apparatus. Such an FEP compression ring further secures the access means to the end of the tube. If the FEP shrink-wrap material is heated slightly above its melting point for an extended period of time, i.e. about 20–60 seconds, the material can melt and flow into the pores of the stretched polytetrafluoroethylene material and contact the FEP material wrapped around the first portion of the access means that will have also melted. Once these two melted FEP thermoplastic materials are in contact with one another, they flow together to form a continuous band of FEP from the outer surface of the first portion of the access means, through the stretched polytetrafluoroethylene material of the tubular component to the outer FEP shrink-wrap coating. The resulting construction has a very strong, air-tight, bond between the access means and the tubular component of the present invention.

Alternatively, an access means can be fabricated by injection molding of a fitting onto the end of a stretched polytetrafluoroethylene tubular apparatus using techniques known to those skilled in the art as insert molding. Insert injection molding of an access means on the end of a tubular apparatus involves first placing a cylindrical piece of tooling into the luminal space of the tube followed by placement of the tube end and the cylindrical tool into a mold cavity. The mold cavity is then filled with a polymeric substance comprised of a thermosetting resin such as polydimethylsiloxane, for example, or with a molten thermoplastic such as fluorinated ethylene propylene (FEP), polycarbonate, polyester, or polysulfone, either alone or in combination, for example. Following curing of the polymeric resin through appropriate reaction conditions or through cooling as required, the mold cavity is opened and the cylindrical mold insert removed from the lumen of the tube. This is a preferred method due to the smooth transition between the luminal surfaces of the connector and the tube.

An access means can also be a hole in the porous polymeric material with one or more flexible pieces, or flaps, of porous polymeric material positioned to cover and close the hole. The flaps may be formed as part of the apparatus or may be attached to the apparatus subsequent to its initial construction.

An access means comprising a resealable port can be repeatedly opened and closed with a sealing means. Sealing means include, but are not limited to, caps, plugs, clamps, compression rings, or valves, for example. The sealing means may be attached to the access means with friction, by clamping, or with screw means comprised of threads and grooves, for example. Depending on the intended use of the apparatus, the access means is sealed with a sealing means to create a hermetical seal, a fluid-tight seal, or a non-fluid-tight seal. An apparatus intended for permanent or long term (i.e. at least about three weeks) implantation in a recipient, is preferably sealed with a hermetical or a fluid-tight seal.

Suitable materials for constructing the access and sealing means include, but are not limited to, metallic, ceramic, glassy, elastomeric, or other polymeric materials, either alone or in combination. Examples of metallic materials include, but are not limited to, tantalum, cobalt-chrome alloys, titanium and its alloys, stainless steel, or gold, either alone or in combination. Examples of ceramic materials include, but are not limited to, aluminas, silicas, zirconias, calcium sulfates, calcium carbonates, calcium phosphates (including hydroxyapatite and beta -tricalcium phosphate), borosilicate glasses, elemental carbon, ALCAP (a ceramic comprising aluminum, calcium, and phosphorous oxides), and bioglasses, either alone or in combination. Examples of elastomeric materials include, but are not limited to silicone, polyurethanes, fluoropolymer rubbers (e.g. Viton), poly (ethylene-co-propylene), and polybutadiene and its copolymers (e.g. Buna-N), either alone or in combination. Examples of polymeric materials include, but are not limited to polytetrafluoroethylene, polyethylene, polypropylene, polystyrene, poly(tetrafluoroethylene-co-perfluoropropylene), polyesters, such as, poly(ethylene terephthalate), polycarbonates, poly(methyl methyacrylate), and polyamides, either alone or in combination. The primary structural requirement of these materials in an access or sealing means is that they have the strength, biocompatibility, and longevity to function permanently or for a long term (i.e. at least about three weeks) in a recipient.

Many of the materials used to construct an apparatus of the present invention are inherently radio-opaque. Those materials that are not inherently radio-opaque can be modified to be radio-opaque by impregnation of the material with barium, for example. Other suitable methods for rendering a material radio-opaque are known to those skilled in the art. The radio-opacity of materials used to construct an apparatus of the present invention is mainly used to facilitate surgical placement of the apparatus or to locate the apparatus in a recipient following implantation.

Figure 9A:
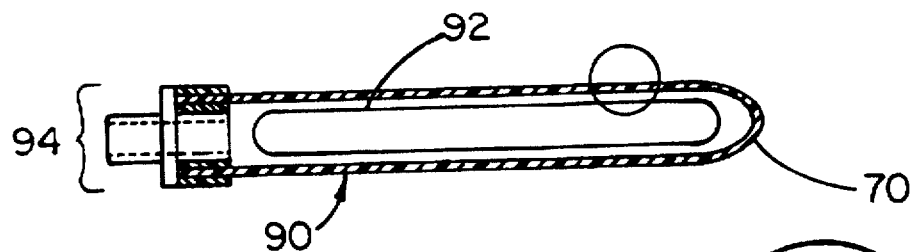
FIG. 9A illustrates a tubular embodiment of the present invention (90) for containing a generally cylindrically shaped therapeutical device (92) using the microporous polymeric material (70) illustrated in FIG. 7, having an access means (94) attached to one end of the tube.
Figure 9C:
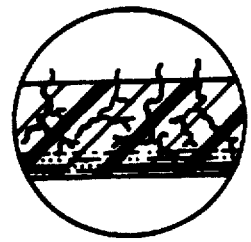
FIG. 9C is an enlargement of the circled area of FIG. 9A.

In a preferred embodiment, an apparatus of the present invention is in the form of an implantable tube for containing a generally cylindrically shaped therapeutical device. The implantable tube is made of a stretched polytetrafluoroethylene material having a cell permeable zone extending from the exterior surface of the tube through to a cell exclusion zone within the material adjacent to and continuous with the luminal surface of the tube. (See FIG. 9A) The cell permeable zone is sufficiently porous for capillaries to form therein. In some tubular embodiments of the present invention, open ends of the tube can be prevented from collapsing with a stent, or core. The stent can be in any shape and made of any biocompatible material suitable for keeping all or part of tubular apparatus in an opened, or expanded, tubular form during storage and/or following implantation. Suitable materials for a stent include, but are not limited to, stainless steel, titanium, and hydrogels. To maintain the entire length of a tubular apparatus in an expanded configuration, an inert core simulating the shape and resilience of a therapeutical device is placed in the apparatus.

The preferred material for such an inert core is HYPAN® Structural Hydrogel. (Hymedix International, Inc., Dayton, N.J.)

Preferably, the material for the tube is a laminate of at least two layers of a stretched polytetrafluoroethylene material each having different porosities. In this embodiment, the portion of the laminate containing the cell exclusion zone is a layer of stretched polytetrafluoroethylene material that is a very thin, very strong non-woven web composed substantially of fibrils in which there are essentially no nodes. This layer has an average pore size ranging between about 0.05 and about 0.4 microns, as measured by porometry. The preferred pore size of this material for use in the present invention is about 0.4 microns in its laminated, or finished, form. The thickness of the material in its finished form is between about 1 micron and about 25.4 microns. The preferred method of making this layer of the laminate utilizes a portion of a method taught by Bacino in U.S. Pat. No. 5,476,589 and corresponding PCT Application Serial No. PCT/US95/07003, filed Jun. 2, 1995, entitled "Porous PTFE Film And A Manufacturing Method Therefor," which is incorporated herein by reference. In the Bacino method, after the appropriate polytetrafluoroethylene starting materials are chosen and prepared as a coagulated dispersion of fine powder polytetrafluoroethylene, the coagulated dispersion powders are lubricated with a hydrocarbon extrusion aid, preferably as odorless mineral spirit such as Isopar K (made by Exxon. Corp.). The lubricated powder is compressed into cylinders and extruded in a ram extruder to form tapes. Two or more layers of tape can be stacked together and compressed between two rolls. The tape or tapes are compressed between rolls to an appropriate thickness, e.g. 5 to 40 mils, or so. The wet tape is stretched transversely to 1.5 to 5 times its original width. The extrusion aid is driven off with heat. The dried tape is then expanded, or stretched, longitudinally between banks of rolls in a space heated to a temperature that is below the polymer melting point of 327° C. The longitudinal expansion is such that the ratio of speed of the second bank of rolls to the first bank is 10–100 to 1, preferably 35 to 1. The longitudinal expansion is repeated at a 1–1.5 to 1 ratio.

Next, the tape, after the longitudinal expansion, is expanded transversely at a temperature that is less than 327° C. to at least 1.5 times and preferably to 6 to 15 times the input width of the original extrudate while restraining the membrane from longitudinal contraction. While still under constraint the membrane is preferably heated to above the polymer melting point of 327° C. and then cooled.

The portion of the laminate containing the cell permeable zone is a stretched polytetrafluoroethylene material made in accordance with the teachings of U.S. Pat. Nos. 3,953,566 and 4,187,390, both issued to Gore, each of which is incorporated herein by reference. The material has an average pore size greater than about 3.0 microns, preferably greater than about 5.0 microns, as measured by fibril length. The thickness of the material ranges from about 10 microns to about 1000 microns, preferably about 40–60 microns.

Lamination of these two different stretched polytetrafluoroethylene materials is performed by repeating some of the steps of the above-referenced Bacino method. To perform the lamination, both above-described stretched polytetrafluoroethylene materials are held together and expanded longitudinally between banks of rolls in a space heated to a temperature that is below the polymer melting point of 327° C. The longitudinal expansion is such that the ratio of speed of the second bank of rolls to the first bank is 10–100 to 1, preferably 35 to 1, for the material produced by the Bacino method. The longitudinal expansion is repeated at a 1–1.5 to 1 ratio, between the second and third set of rolls where the material of the '566 patent is joined with the material from the Bacino method.

Next, the laminate, after the longitudinal expansion, is expanded transversely at a temperature that is less than 327° C. to at least 1.5 times and preferably to 6 to 15 times the input width of the original laminates while restraining the laminate from longitudinal and transverse contraction. While still under constraint the laminate is preferably heated to above the polymer melting point of 327° C. and then cooled.

Figure 19:
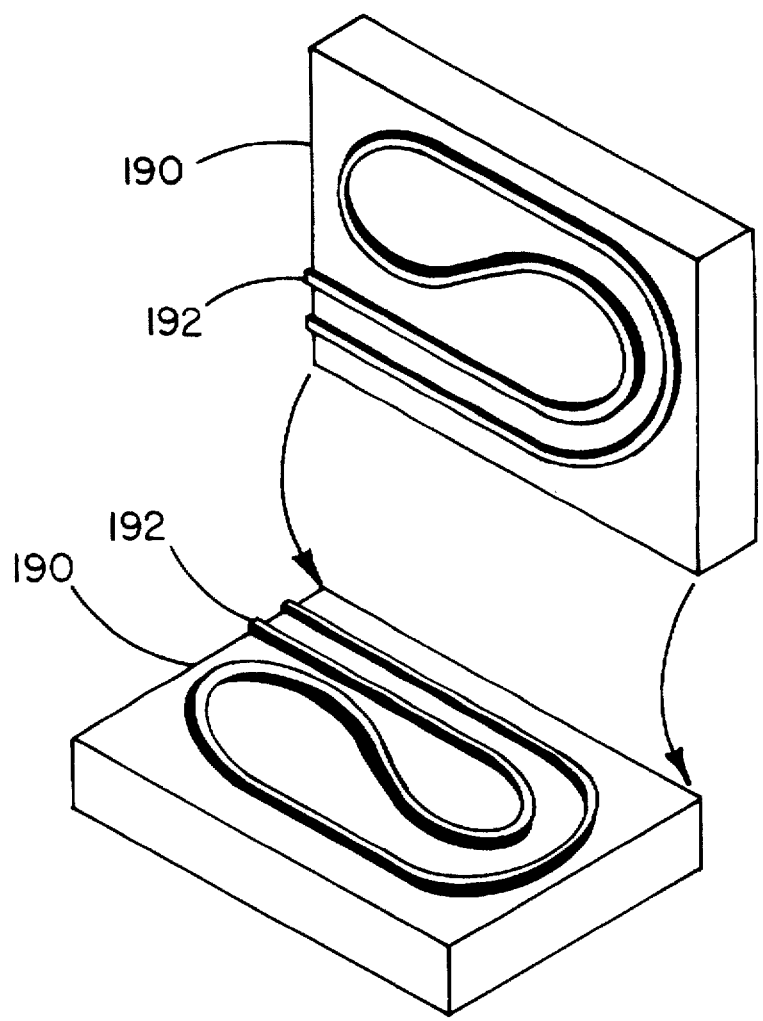
FIG. 19 illustrates a pair of dies (190) having raised tracks (192) elevated above the surface each member of the die pair.

A preferred method of making a tubular form of the present invention from this laminate is by attaching portions of two or more planar sheets of the laminate together with heat and pressure. Heat and pressure are preferably applied to layers of the laminate with a metal die having elevated tracks raised above the surface of the die in a pattern that defines, or reflects, the perimeter of most, or all, of the tubular form. (See FIG. 19, for example) The raised tracks concentrate the heat and pressure used to attach the laminates together. A thermally and chemically stable core is usually placed between the layers of laminate in the die within the pattern defining the perimeter of the tubular form of the apparatus to aid in forming the tubular form of the construction. Dies can be made that produce tubes in essentially any shape that permits easy placement and replacement of a therapeutical device in the invention. It is understood that this method is not confined to making tubular forms, but is applicable to other geometric and/or irregular shapes.

To make a tubular form with two planar sheets of laminate, the sheets of laminate are first placed together with their respective cell exclusion zones facing each other. The laminates are then placed in a die having the desired pattern of raised tracks. A thermally and chemically stable core is placed between the layers of laminate within the perimeter of the tubular form outlined by the elevated tracks in the die. Once in the die, the laminates and the core are heated to between about 310° C. and about 380° C. for about 1–10 minutes at a pressure sufficient to densify the stretched polytetrafluoroethylene material and attach the planar sheets of laminate together where the heated tracks contact the sheets of laminate. The tube, core, and attached planar material are allowed to cool to room temperature and then removed from the die. The core is released from the interior of the tubular form by injecting water between the core and wall of the tube with a hypodermic syringe, for example. The planar material attached to the apparatus after its construction can be left attached, trimmed, or removed. Planar material left attached to the apparatus helps to hold the apparatus in the proper shape. The planar material also provides a surgeon with a means of handling the apparatus and a means of attaching an apparatus securely to an implantation site in a recipient. (See FIG. 18, for example)

Another way to form an apparatus of the present invention in a tubular shape is by wrapping a material made in accordance with the teachings of Bacino, supra, on a mandrel followed by another wrap of a material made in accordance with the teachings of Gore, supra. Longitudinal and helical orientations of the wrapped film may be used. This construction is then heated from about 320° C. to about 380° C. for about 5–10 minutes to bond the respective materials to themselves and to each other. The overlap of one layer of material with the next layer can range from less than about 10% to about 50%. In many applications, the overlap is preferably about 10%. It is understood that wraps and laminates of these materials can have no overlap between layers, however. In such an embodiment, the edge of each successive wrap of material abuts the edge of the previous wrap of material.

Figure 9B:
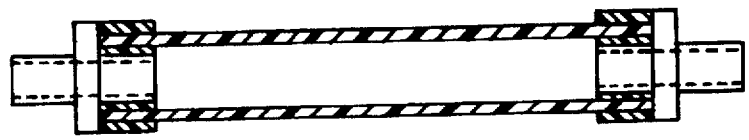
FIG. 9B illustrates the embodiment illustrated in FIG. 9A, but with an access means at each end of the tube.
Figure 11:
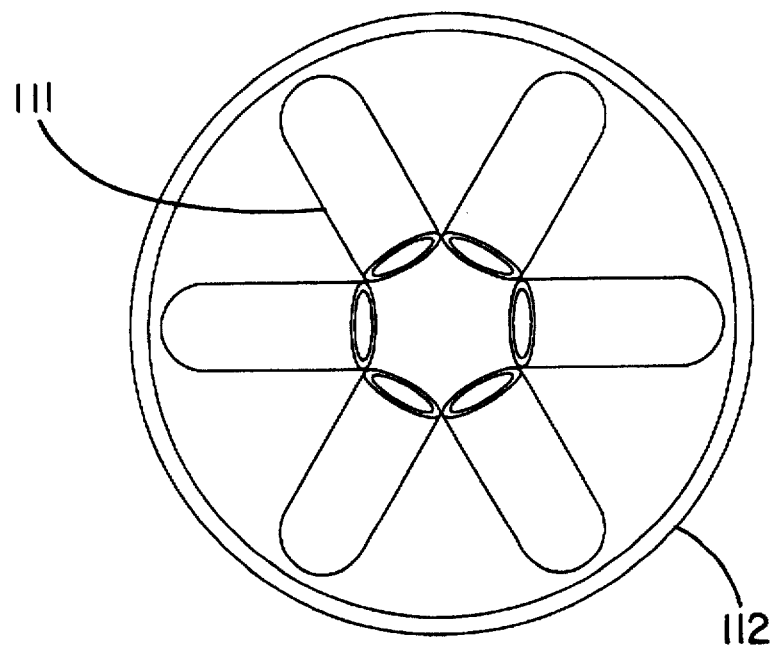
FIG. 11 illustrates an embodiment of the present invention having a plurality of cylindrically shaped containment apparatuses (111) arranged in a radial array attached to a circular planar material (112) to provide a single surgical accession site for the various tubes.
Figure 12:
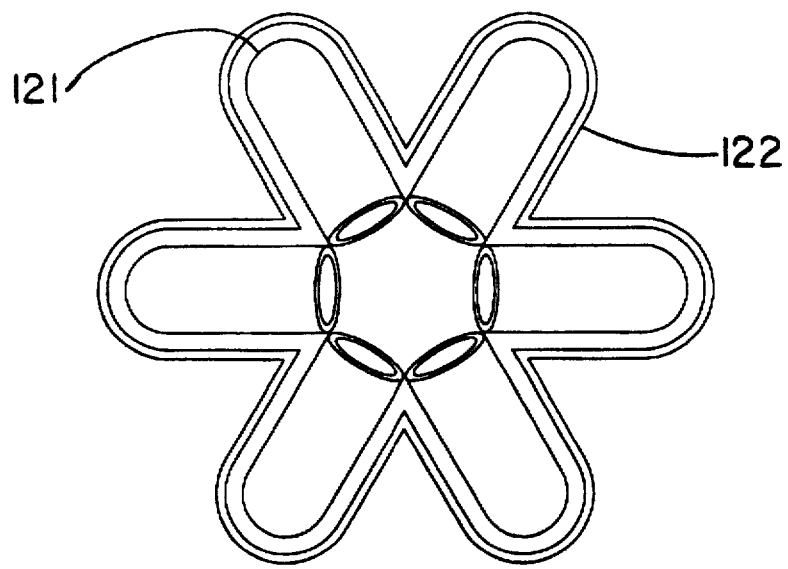
FIG. 12 illustrates an embodiment of the present invention having a plurality of cylindrically shaped containment apparatuses (121) arranged in a radial array attached to a planar material (122) that generally follows the outline of the array to provide a single surgical accession site for the various tubes.
Figure 13:
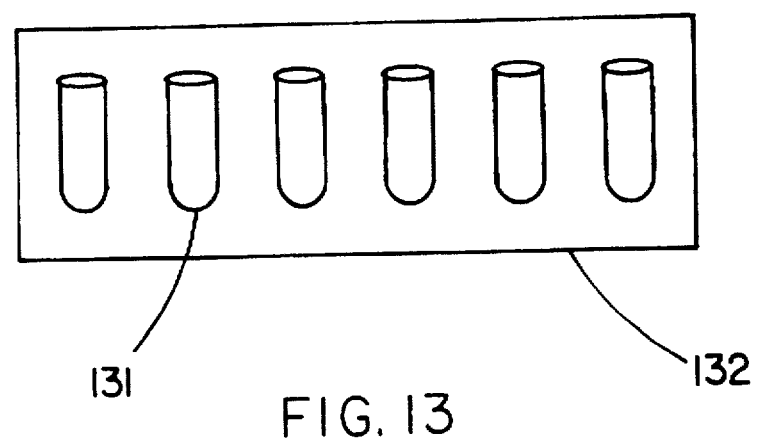
FIG. 13 illustrates an embodiment of the present invention having a plurality of cylindrically shaped containment apparatuses (131) arranged generally parallel to one another and attached to a planar material (132).

In one embodiment, the tube has an access means at one end of the tube through which a therapeutical device is moved in and out of the luminal space of the tube. In another embodiment, the tube has access means at both ends of the tube through either of which a therapeutical device is moved in and out of the luminal space of the tube. (See FIG. 9B) In both embodiments, the access means can be repeatedly sealed, opened, and resealed. In one aspect of this embodiment, the apparatus is in the form of one or more substantially straight tubes having access means at one or both ends of each tube. A plurality of these tubes can be arranged in a configuration that permits multiple therapeutical devices to be placed in a recipient. (See FIGS. 11–13) The therapeutical devices can have the same or different contents. For therapeutical devices having the same contents, the number of therapeutical devices contained in this aspect of the present invention can be varied to more accurately control the dose of the therapeutic substance delivered to the recipient by the device. Therapeutical devices having different contents can be placed in an apparatus of the present invention, thereby permitting more than one therapeutical substance to be administered to a recipient simultaneously or sequentially. If a therapeutical device contained in an apparatus of the present invention fails, or otherwise needs replacement, only the therapeutical device that needs to be replaced is replaced. In another aspect of this embodiment, a tube having access means on both ends of the tube is permanently held in the shape of at least one loop with a piece of planar material either attached to, or integral with, the porous polymeric material of the tube. In this aspect, the access means are positioned and maintained sufficiently close to one another with a holding means so that the apparatus is implantable and accessible for filling and refilling with a therapeutical device at a single site in a recipient. (See FIG. 14)

In order to easily place and replace a therapeutical device in a tubular apparatus of the present invention, a slippery, or lubricous, surface should be present on both the exterior surface of the therapeutical device and the inner surface of the present invention. The stretched polytetrafluoroethylene material used to construct the present invention is lubricous. Stretched polytetrafluoroethylene in combination with a hydrogel used to form the cell exclusion zone in the apparatus makes the luminal surface of the tube even more slippery. The selectively permeable polymeric materials of most therapeutical devices are also lubricous. Such a membrane impregnated with a hydrogel material or coated with a surfactant is more lubricous. Together, the inner surface of a tubular apparatus of the present invention and a lubricous exterior surface of a therapeutical device are very lubricous with respect to each other. This permits a therapeutical device to be easily placed and replaced in a tubular apparatus of the present invention. A therapeutical device can be manipulated in and out of an apparatus of the present invention with forceps and the like. For an apparatus of the present invention having access means at both ends of the tube, a therapeutical device is optionally inserted into and removed from the luminal space of a tubular apparatus of the present invention with a fluid stream.

In addition to the importance of having lubricous surfaces between the interior surface of a tubular apparatus of the present invention and the external surface of a therapeutical device during insertion and retrieval of the device from the apparatus, when doing so with a fluid stream it is also important to have sufficient clearance between these components to accommodate the fluid stream and the therapeutical device entrained therein during loading, retrieval, and replacement of the device. To this end, the selectively permeable porous polymeric material of the tubular portion of the apparatus is radially distensible. Suitable radially distensible materials can stretch slightly under pressure and return to their original dimensions when the pressure is released. Very close or direct contact between the interior surface of an apparatus of the present invention and the external surface of a therapeutical device along substantially the entire length of the therapeutical device can be achieved with this type of material.

Alternatively, the inner diameter of the tubular portion of the apparatus can be made larger than the outer diameter of the therapeutical device the apparatus is intended to contain. When this construction is implanted, vascularized, if desired, and loaded with a therapeutical device, all, or most, areas of the tubular portion of the apparatus collapses against the therapeutical device contained therein. This results in direct contact between the interior surface of the apparatus and the external surface of the therapeutical device along substantially the entire length of the therapeutical device. Even if direct contact is not achieved, the desired result can be obtained if the space that remains between the external surface of the therapeutical device and the interior surface of the tubular portion of the apparatus is occupied by a material, or stagnate fluid layer, of sufficient diffusive permeability to solutes and products to maintain the necessary rate of mass transport across the wall of the tube. Suitable materials for this purpose include, but are not limited to, alginate, agar, a hydrogel, such as those TN grades of hydrogel from Hymedix International, Inc., Dayton, N.J., or a thermoreversible gel, such as those taught by Chick et al. in U.S. Pat. No. 5,116,494, which is incorporated herein by reference. The apparatus is collapsed against the therapeutical device primarily by the wound healing tissues of the implantation site. Suitable porous polymeric materials for either of these embodiments include those listed above, as well as, similar materials having elastomeric components incorporated therein.

Figure 15A:
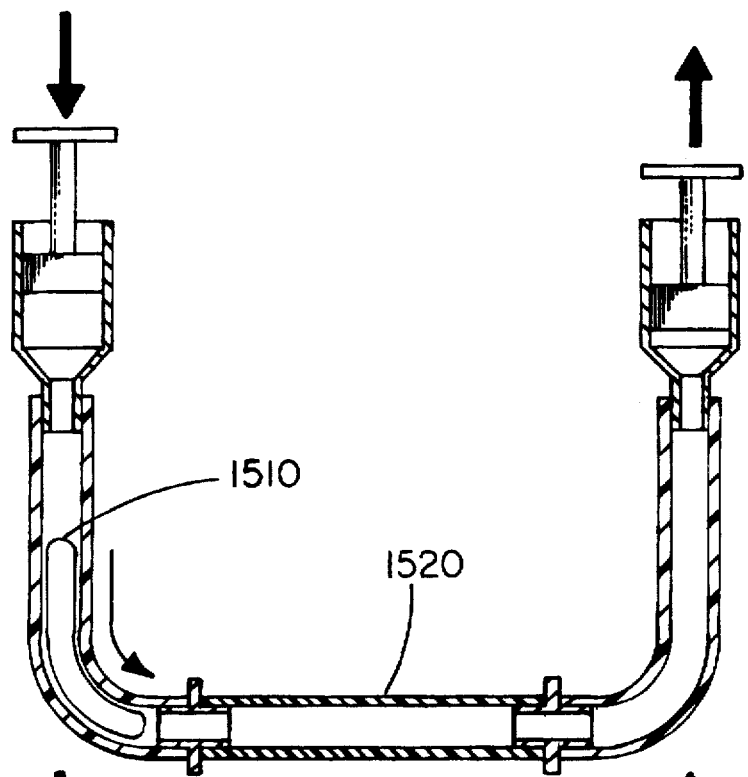
FIGS. 15A and 15B, respectively, illustrate a method of placing and removing a therapeutical device (1510) in a tubular apparatus of the present invention (1520) with a fluid stream.

A therapeutical device is placed in a tubular apparatus of the present invention with a fluid stream by first opening both access means of the tube. A means of establishing a pressurized fluid stream through the luminal space of the apparatus is attached to one of the access means of the tube. A means of receiving the fluid stream is attached to the other access means of the tube. A fluid stream is established in the luminal space of the apparatus by causing fluid flow into the appropriate access means and concurrently out of the other access means. This can be accomplished by pumping fluid at positive pressure into one of the access means. To place a therapeutical device in the apparatus, a therapeutical device is first entrained in a pressurized fluid stream and then inserted into the tube with the fluid stream. Once the therapeutical device is placed in the tube, the fluid stream is discontinued. When the fluid stream is discontinued, the exterior surface of the therapeutical device contained in the tube and the interior surface of the tube are preferably in direct contact. The access means are then closed and the assembly put to use. (See FIG. 15A)

Figure 15B:
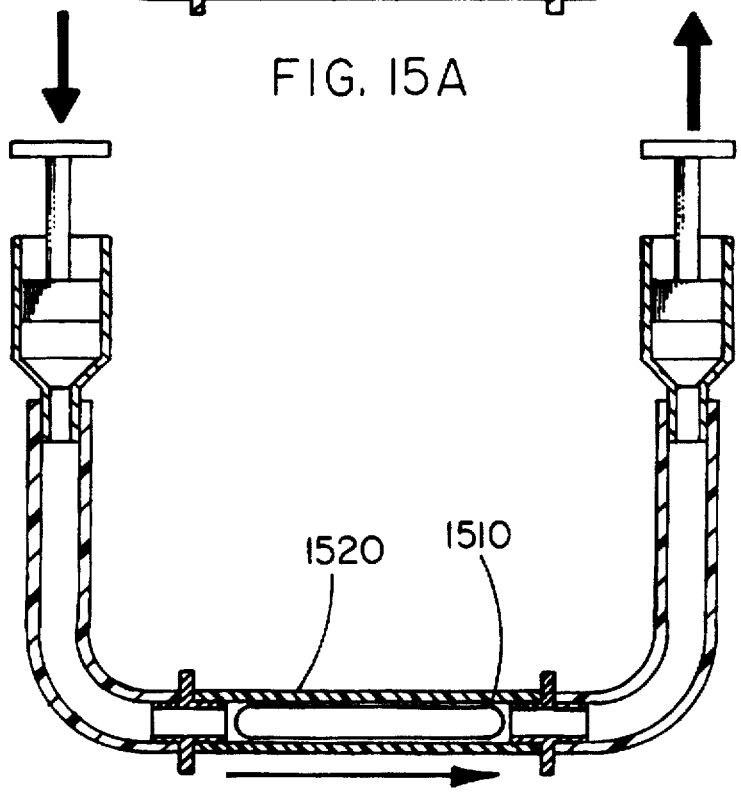

Removal of a therapeutical device from a tubular apparatus of the present invention is accomplished by opening both access means on the tube and attaching a means of providing a pressurized fluid stream to one of the access means. A pressurized fluid stream is then established around the therapeutical device and through the luminal space of the tube to entrain the device in the fluid stream. Once entrained in the fluid stream in the tube, the therapeutical device is removed from the tube through one of the access means with the fluid stream. The fluid stream can either push or pull the therapeutical device out of the apparatus. (See FIG. 15B) If desired, another therapeutical device can be placed in the apparatus by repeating the appropriate insertion steps outlined above. In addition to ease of insertion and retrieval of a therapeutical device contained in an apparatus of the present invention, the present invention has the advantage of preserving tissues associated with the selectively permeable material of the apparatus from damage during placement and exchange of a therapeutical device in the apparatus.

Care should be taken to avoid collapsing the tube during insertion or removal of a therapeutical device. Maintaining internal positive pressure in a range of about 5–100 psi (i.e. about $3.45 \times 10^4$ N/m$^2$ to about $6.89 \times 10^5$ N/m$^2$) is usually adequate to prevent collapse of the tube during loading, unloading, and refilling of the tube with a therapeutical device. The thickness and nominal diameter of a porous polymeric membrane will depend in large part on how much internal pressure a particular containment apparatus of the present invention will tolerate.

When a therapeutical device is contained in an apparatus of the present invention, the minimum permissible clearance between the exterior surface of the therapeutical device and the interior surface of the apparatus depends in large part on the particular therapeutical device embodiment and the therapy sought to be achieved with the device. For example, cell encapsulation devices implanted in a recipient have a bi-directional flux of solutes between cells in the cell encapsulation device and tissues of the recipient. To maintain a rate of flux sufficient to sustain the viability of the encapsulated cells and to effect the desired therapeutical result, cell encapsulation devices contained in an apparatus of the present invention usually require very small clearances in a range of about 0.5–50 microns or direct contact between the permeable surface of the device and the interior surface of the containment apparatus. Drug delivery and gene therapy devices may not have the same flux rate requirements as a cell encapsulation device for transport of the particular therapeutical substance from the device to tissues of a recipient. Accordingly, drug delivery and gene therapy devices for use with the present invention may not need the minimal clearances required by cell encapsulation devices.

Cell encapsulation devices suitable for use in conjunction with the present invention preferably are devices of the type disclosed in the patent application of Butler et al., PCT/US94/07190, entitled "Cell Encapsulation Device," which is incorporated herein by reference. Butler et al. disclose a cell encapsulation device that is generally cylindrical in geometry with a flexible cell displacing core enclosed in a selectively permeable membrane. The selective permeability of the membrane can be adjusted by impregnating the membrane with an appropriate hydrogel material. The cell displacing core positions the encapsulated cells in direct, or near direct, contact with the selectively permeable membrane. The encapsulated cells are positioned in the device at a distance from a nutrient source and at a cell density that minimizes the diffusion distance biochemical substances must traverse between each encapsulated cell and the external environment of the device. This configuration enables a maximum number of encapsulated cells to be maintained in a given volume at high levels of viability and productivity. The selectively permeable membrane contains cells within the device while permitting exchange of biochemical substances between the encapsulated cells and the exterior surface of the device. In a situation where the cell encapsulation device is embedded in a recipient and contains allogeneic or xenogeneic cells, the selectively permeable membrane also serves to isolate the encapsulated cells from the immune system of the recipient.

Cell encapsulation devices of the type disclosed by Butler et al. are suitable for use as implantable therapeutic product delivery systems, implantable artificial organs, or bioreactors. A containment apparatus of the present invention, in conjunction with cells in a cell encapsulation device of the type disclosed by Butler et al., can also function as an implantable therapeutic product delivery system, an implantable artificial organ, or a bioreactor. A preferred use of the present invention, in conjunction with a cell encapsulation device of the type disclose by Butler et al., is as an artificial pancreas. In any one of these utilities, the containment apparatus of the present invention enables a complete cell encapsulation device and its entire cache of cells to be easily inserted, retrieved, and replaced in the apparatus as a unit.

Figure 16:
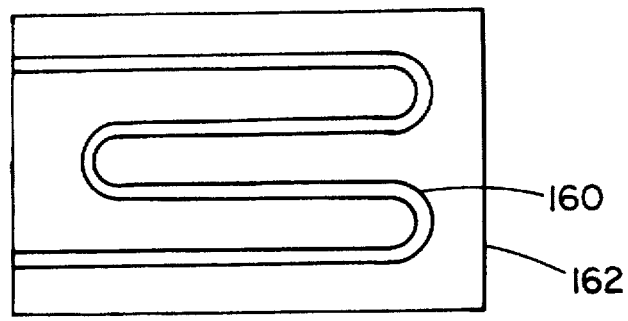
FIG. 16 illustrates a tubular form of the present invention curved into a plurality of convolutions (160) and held in shape by a planar material (162).
Figure 17:
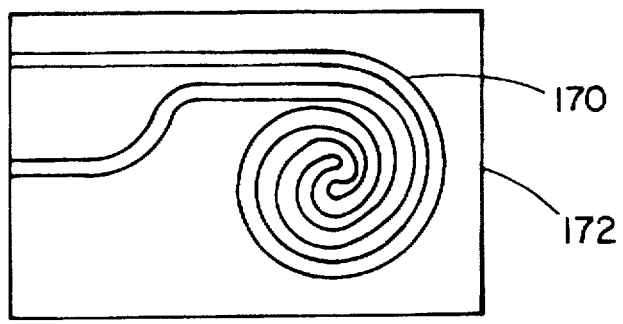
FIG. 17 illustrates a tubular form of the present invention curved into a generally spiral shape (170) and held in shape by a planar material (172).

Cell encapsulation devices of the type disclosed by Butler et al., supra, are often several decimeters in length. In order to confine the space occupied by such lengthy cell encapsulation devices to a useful size for surgical implantation, a tubular form of a containment apparatus of the present invention is curved into a plurality of convolutions and permanently held in shape by a planar material. (See FIG. 16) Alternatively, the apparatus can be wound into a spiral shape and attached to a planar material. (See FIG. 17) Any geometry that serves to confine the space occupied by the apparatus while permitting a cell encapsulation device to be easily placed and replaced in the apparatus is suitable for use in the present invention, however. (See FIG. 18, for example) By maintaining the containment apparatus in a gently convoluted conformation, twisting, kinking, or other extreme bending of a therapeutical device contained therein is minimized or eliminated. Such distortion of a therapeutical device contained in an apparatus of the present invention can damage the device and/or make removal of the device from an apparatus difficult or impossible. The planar material can be attached to the apparatus subsequent to its construction or as part of the initial construction of the apparatus, as described above.

The planar material also serves as a means for handling an apparatus of the present invention during surgical implantation. In addition, the planar material is a means through which the apparatus is surgically anchored to tissues of a recipient so the implanted apparatus maintains its curved shape and does not move from the implantation site. Preferably, the planar material is made of a flexible porous polymeric material. Most preferably, the planar material is the same porous polymeric material used to construct the tubular portion of the apparatus and is continuous therewith.

A drug delivery device suitable for use in conjunction with the present invention includes, but is not limited to, NORPLANT® contraceptive subdermal implant. (The Population Council, Inc., New York, N.Y.) An apparatus of the present invention suitable for use with the NORPLANT® contraceptive subdermal implant device can have one or more access means. The NORPLANT® contraceptive subdermal implant device can be inserted, removed, and replaced in an apparatus of the present invention with a fluid stream, by using surgical forceps, or manually.

Gene therapy devices are much like drug delivery devices in that they impart a therapeutic agent to a recipient unidirectionally from the interior of the device to tissues of the recipient. Any of the above-described geometries, or combinations thereof, may be used for an apparatus of the present invention in conjunction with a gene therapy device. It is understood, however, that customized shapes may be needed to perform gene therapy in particular parts of a recipient's anatomy. Manipulation of a gene therapy device in and out of an apparatus of the present invention can be accomplished with a fluid stream, a catheter system, or surgical forceps, for example.

Without intending to limit the scope of the present invention, the following examples illustrate how the present invention can be made and used.

EXAMPLES

Example 1

With the following method, an apparatus of the present invention may be made in essentially any shape that permits easy placement and replacement of a therapeutical device in the apparatus. This example describes the construction of a tubular form of the apparatus wherein the tube generally follows the path illustrated in FIG. 9A. The tubular portion of the apparatus has a planar material attached to the tube to hold the tube in its path and to provide anchorage sites for attaching the apparatus to the implantation site. Construction of this embodiment is described as follows.

The starting material for the apparatus is a laminate of two layers of stretched polytetrafluoroethylene materials each having different porosities. In this embodiment, the portion of the laminate containing the cell exclusion zone is a layer of stretched polytetrafluoroethylene material that is a very thin, very strong non-woven web composed substantially of fibrils in which there were essentially no nodes. This layer has an average pore size of about 0.4 microns, as measured by porometry, and a thickness of about 1 micron in its laminated, or finished, form. The method of making this layer of the laminate utilized a portion of a method taught by Bacino in U.S. patent application Ser. No. 08/403,232 and corresponding PCT Application Serial No. PCT/US95/07003, filed Jun. 2, 1995, entitled "Porous PTFE Film And A Manufacturing Method Therefor," which is incorporated herein by reference. After the appropriate polytetrafluoroethylene starting materials were chosen and prepared as a coagulated dispersion of fine powder polytetrafluoroethylene in accordance with the teachings of Bacino, the coagulated dispersion powders were lubricated with the hydrocarbon extrusion aid Isopar K (made by Exxon. Corp.). The lubricated powder was compressed into cylinders and extruded in a ram extruder to form tapes. Three layers of tape were stacked together and compressed between two rolls. The tapes were compressed between rolls to an appropriate thickness of about 15 mils. (375 microns) The wet tape was stretched transversely to about 3.5 times its original width. The extrusion aid was driven off with heat. (i.e. about 260° C.) The dried tape was then expanded, or stretched, longitudinally between banks of rolls in a space heated to a temperature that was less than 327° C., i.e. about 305° C. The longitudinal expansion was such that the ratio of speed of the second bank of rolls to the first bank was 33 to 1. The longitudinal expansion was repeated at a 1.5 to 1 ratio.

Next, the tape, after the longitudinal expansion, was expanded transversely at a temperature that was less than 327° C., i.e. about 305° C., at eleven (11) times the input width of the original extrudate while restraining the membrane from longitudinal contraction. While still under constraint the membrane was heated to above the polymer melting point of 327° C., i.e. about 365° C. and then cooled to room temperature.

The portion of the laminate containing the cell permeable zone was a stretched polytetrafluoroethylene material made in accordance with the teachings of U.S. Pat. Nos. 3,953,566 and 4,187,390, both issued to Gore, each of which is incorporated herein by reference. The material has an average pore size greater than about 5.0 microns, as measured by fibril length, and a thickness of about 30 microns.

Lamination of these two different stretched polytetrafluoroethylene materials was performed by repeating some of the steps of the above-referenced Bacino method. To perform the lamination, both above-described stretched polytetrafluoroethylene materials were held together and expanded longitudinally between banks of rolls in a space heated to a temperature that was below the polymer melting point of 327° C., i.e. about 305° C. The longitudinal expansion was such that the ratio of speed of the second bank of rolls to the first bank was 33 to 1 for the material produced by the Bacino method. The longitudinal expansion was repeated at a 1.5 to 1 ratio, between the second and third set of rolls where the material of the '566 patent was joined with the material from the Bacino method.

Next, the laminate, after the longitudinal expansion, was expanded transversely at a temperature that was less than 327° C., i.e. about 305° C., to 11 times the input width of the original laminates while restraining the laminate from longitudinal and transverse contraction. While still under constraint the laminate was heated to above the polymer melting point of 327° C., i.e. about 365° C., and then cooled to room temperature.

A tubular form of the present invention using this laminate was made by attaching two planar sheets of the laminate together along a line that defines the perimeter of the tubular form. The sheets of laminate were attached with heat and pressure using a pair of stainless steel machined dies having opposing raised tracks on each member of the die pair. The elevated tracks generally reflect the pattern depicted in FIG. 9A. To make the tubular form, two sheets of laminate were first held together in the die with their respective cell exclusion zones facing each other. A tubular core made of full density polytetrafluoroethylene was placed between the layers of laminate within the outline of the perimeter defined by the elevated tracks prior to the heating and pressing process. Once in the die, the laminates were placed in a pneumatic press with platens pre-heated to about 320° C. for about 10 minutes at a pressure sufficient to densify the stretched polytetrafluoroethylene material. When brought together under heat and pressure, the elevated opposing tracks of the dies joined the layers in the areas contacted by the raised tracks. The tube, core, and attached planar material were allowed to cool to room temperature and then removed from the die. The core was removed from the interior of the tubular portion of the apparatus by injecting water between the core and the wall of the tube with a hypodermic syringe. The joined portions of the construction formed the perimeter of the tube except for one end that remained open in order to receive a therapeutical device. The tube thus formed was about 5.08 cm long and an inner diameter of about 0.16 cm, with one closed and one open end. The planar material that remained attached to the apparatus after its construction was left attached.

An access means was attached to the open end of the tube as follows. A rod made of full density polytetrafluoroethylene was machined into a hollow tubular configuration about 0.94 cm long comprising three main portions having an inner diameter of about 0.1 cm. The first portion has an outer diameter of about 0.16 cm, a length of about 0.30 cm, and fits snugly inside the end of the tubular component of the apparatus. The second portion has an outer diameter of about 0.2 cm, a length of about 0.20 cm and functions as an abutment for the tube and the sealing means. The third portion has an outer diameter of about 0.16 cm, a length of about 0.30 cm and serves to receive and retain a sealing means.

A 2.0 mm nominal inner diameter piece of fluorinated ethylene propylene (FEP) shrink-tube was placed over the first portion of the access means, trimmed to length, and heated with a hot air gun to a temperature sufficient to shrink the FEP in place. The open end of the above-described tube was stretched slightly and gently placed over the FEP coated first portion of the access means up to the second portion of the access means. A second piece of FEP shrink-tube was placed over the tube above the underlying FEP coated first portion of the access means. (See FIG. 8, for example) The second piece of FEP was heated with a hot air gun to a temperature sufficient to shrink the FEP over the tube. Hot air was also used to partially melt both the inner and the outer layers of FEP shrink-tube thereby forming a strong bond between the stretched polytetrafluoroethylene tube and the access means.

It is understood that access means can be attached to both ends of a tubular apparatus by modifying the above-described procedure to accommodate a tube having both ends open.

Example 2

Figure 18:
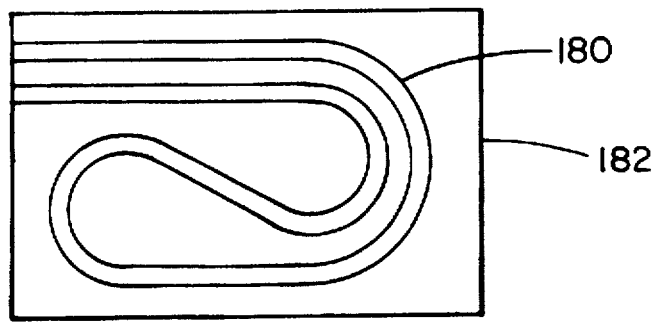
FIG. 18 illustrates a tubular form of the present invention curved into a meandering shape (180) and held in shape by a planar material (182).

A tubular apparatus of the present invention having the pattern depicted in FIG. 18 was made with the same procedure described in Example 1.

Example 3

Another tubular form of the present invention made of stretched polytetrafluoroethylene materials having a cell permeable zone beginning at the exterior surface of the tube and continuing across the thickness of the tube through to a cell exclusion zone within the material adjacent to and continuous with the interior, or luminal, surface of the material is made as follows. The stretched polytetrafluoroethylene material is a laminate of two stretched polytetrafluoroethylene planar materials. The first stretched polytetrafluoroethylene material having a cell permeable zone with an average pore size of about 0.4 microns, as measured by porometry, and thickness of about 1 micron was made in accordance with the teachings of Bacino in U.S. patent application Ser. No. 08/403,232 and corresponding PCT Application Serial No. PCT/US95/07003, filed Jun. 2, 1995, entitled "Porous PTFE Film And A Manufacturing Method Therefor" (hereinafter "Bacino material"), which is incorporated herein by reference. The second stretched polytetrafluoroethylene material having the cell exclusion zone with an average pore size of about 5.0 microns, as measured by fibril length, and thickness of about 30 microns was made in accordance with the teachings of U.S. Pat. Nos. 3,953,566 and 4,187,390, both issued to Gore (hereinafter "Gore material"), each of which is incorporated herein by reference. Once obtained, both the Bacino and the Gore materials were individually spooled onto a polypropylene core, about 1.4 cm in diameter, and then slit lengthwise with a razor blaze to a width of about 0.93 cm. The Bacino material was then wrapped onto a highly polished 2.0 mm diameter mandrel in a substantially helical fashion having an overlap of about 0.32 cm from one layer of wrap to the next. The Gore material was wrapped onto the Bacino material in a helical fashion having an overlap of about 0.32 cm from one layer of wrap to the next.

This construction was then placed in an oven set to about 380° C. for about seven (7) minutes to bond the wrapped layers of the Bacino and Gore materials to themselves and to bond the Bacino material and the Gore material together to form a laminate. The laminate was then allowed to cool to room temperature before gently removing it from the mandrel. The laminate was removed from the mandrel by gently massaging it free in a twisting motion.

Access means are attached to one or both ends of the tube as described in Example 1.

Example 4

A tubular apparatus of the present invention having an essentially confluent cell exclusion zone formed with a thermoplastic hydrogel material impregnated within the porous structure of a stretched polytetrafluoroethlyene material adjacent to and continuous with the luminal surface of the tube was made as follows. A laminate of stretched polytetrafluoroethylene materials made in accordance with the teachings of Gore, supra, having an average pore size at the luminal surface of about 5 microns, as measured by porometry, a fibril length of about 60 microns at the exterior surface of the material, and a thickness of about 600 microns was made into a tubular form. The hydrogel material HYPAN® Structural Hydrogel (10% HN-86 in dimethyl sulfoxide (DMSO)) was impregnated in the stretched polytetrafluoroethylene material with a spool shaped device that delivered the hydrogel material to the luminal surface of the tube as the device is moved through the luminal space of the tube. The outer diameter of the flange portions of the spool shaped device matched the inner diameter of the tube to form a partial seal therewith. The center of the device was hollow and communicated with holes in the indented sides of the spool shaped device. A delivery tube was attached to the hollow center of the device. Prior to impregnating the tube with the hydrogel material, the tube is wetted with DMSO. Following wetting of the tube with DMSO, the device was in place in the lumen of the tube, hydrogel material was pumped through the delivery tube and the spool shaped device to the luminal surface of the tube at a rate of about 7.5 ml/hr. The hydrogel material was under pressure and entered the pores of the stretched polytetrafluoroethylene material adjacent to the luminal surface of the tube to a depth estimated to be between about 10% and 20% of the total thickness of the tube wall. The spool shaped device was moved along the length of the tube at a rate of about 26 cm/min while dispensing hydrogel onto the luminal surface of the tube and into the pores of the stretched polytetrafluoroethylene material. The impregnated hydrogel material was coagulated by injecting deionized water through the luminal space of the tube with a syringe.

Example 5

Eight containment apparatuses of the type described in Example 1, above, were tested in vivo for host response, neovascularization and tissue anchorage to the apparatuses. Test apparatuses were in the form of tubes approximately 2 mm in diameter and about 2.5 cm in length. Each apparatus had a single access means and contained a generally cylindrically shaped resilient core made of HYPAN® Structural Hydrogel HN-80 (Hymedix International, Inc., Dayton, N.J.) to keep the tube from collapsing once implanted and to simulate a therapeutical device contained within the apparatus. The exterior surface of each HYPAN® Structural Hydrogel core was in direct contact with the interior, or luminal, surface of each apparatus along substantially the entire length of the core. Prior to implantation, the apparatuses were steam sterilized at 120° C. for 20 minutes.

The HYPAN® Structural Hydrogel core was made by mixing pellets of the hydrogel material, designated HN-80, at a concentration of about 20% in an aqueous solution of 55% sodium thiocyanate (NaSCN) to create a polymer solution having the consistency of honey. The polymer solution was extruded under water in a waterbath through a round die and taken up by the capstans also mounted under water. The diameter of the die was about 1.4 mm. Once extruded, the hydrogel core was rinsed for about 24 hrs. in distilled water.

On the day of implantation each apparatus was dipped in 100% ethanol for approximately 2 seconds, followed by immersion in phosphate buffered saline pH 7.2 (GibcoBRL) for approximately 10 seconds to remove the ethanol. Due to the hydrophobic nature of the stretched polytetrafluoroethylene this "wetting" procedure is necessary to assure filling of the interstices of the membrane with liquid prior to implantation. The apparatuses remained submerged in fresh phosphate buffered saline until the core was inserted into the lumen of the apparatus through the open end of the tube. The end was sealed with a small band of silicone rubber tubing.

The apparatuses were implanted subcutaneously in four Fischer rats. (Simonson Labs.) Each animal received two subcutaneous implants located on opposite sides of the dorsal midline of the body. To implant each apparatus, an incision was made in the skin of the rat and the subcutaneous tissue was blunt dissected approximately 4 cm just lateral to the dorsal midline. Implants were inserted into subcutaneous pockets and sutured at each end to the subcutaneous tissue using GORE-TEX® CV-5 Suture. (W. L. Gore & Associates, Inc., Flagstaff, Ariz.) The skin incision was closed with a simple interrupted suture. The in vivo responses to the implants were examined at two weeks and six weeks post implantation.

Gross examination of the containment apparatus in situ showed that all apparatuses were anchored to surrounding host tissues at both two and six weeks. None of the apparatuses could be extracted without excision of the surrounding host tissues. This indicates that each apparatus was fully anchored to the surrounding tissues as verified by the subsequent histology.

Histological examination of each apparatus showed that the implants were located in the subcutaneous space most commonly in the loose connective tissue between the cutaneous trunci and superficial skeletal muscles of the back of each rat. At two weeks, trichrome staining showed that host connective tissue had invaded the cell permeable zone of each apparatus to a position adjacent to, but not within, the cell exclusion zone of the apparatus. Many of the cells in the cell permeable zone after two weeks were of the leukocyte lineage. Host vasculature, predominately capillaries, had also invaded the cell permeable zone of the apparatus up to the cell exclusion zone. In each of the apparatuses, capillaries were within about 25 microns of the lumen of the apparatus.

After implantation for six weeks, histologic examination of each explanted apparatus showed fewer leukocytes remaining within the cell permeable zone of the apparatus or in the tissue immediately surrounding the apparatus. This indicates that a chronic inflammatory response was not caused by the implanted apparatus. Host connective tissue and capillaries were still present within the cell permeable zone of the apparatus and could be seen located adjacent to the cell exclusion zone of the apparatus. The majority of host cells present after six weeks were of the fibroblast phenotype and were interspersed among connective tissue fibers that were present within the cell permeable zone of the apparatuses. No cells or connective tissue were present in the cell exclusion zone of the apparatus or in the luminal space of the apparatus. It is believed that the thin, open microstructure of the cell permeable zone of the present invention permits the wound healing response of the implant recipient to create a vascular plexus close to the cell exclusion zone of the apparatus and within about 25 microns of the lumen of the apparatus.

Example 6

Figure 14:
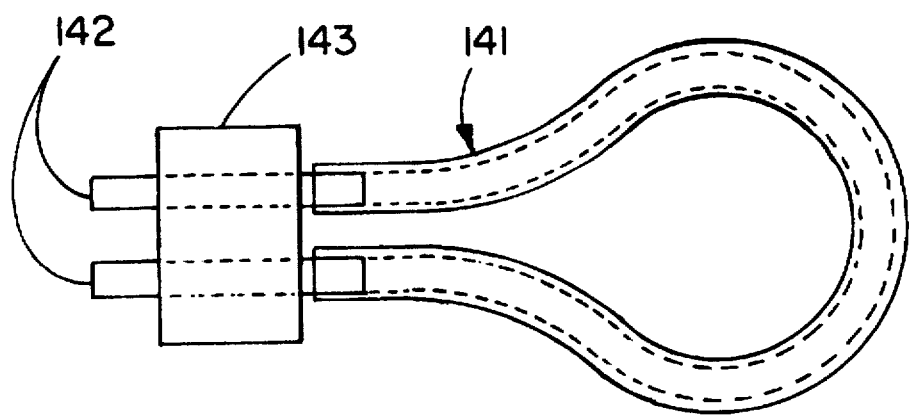
FIG. 14 illustrates a tubular embodiment of the present invention (141) having access means (142) at both ends of the tube, wherein the access means are positioned and maintained sufficiently close together with a holding means (143) so that the apparatus is implantable and accessible at a single site in a recipient.
Figure 15C:
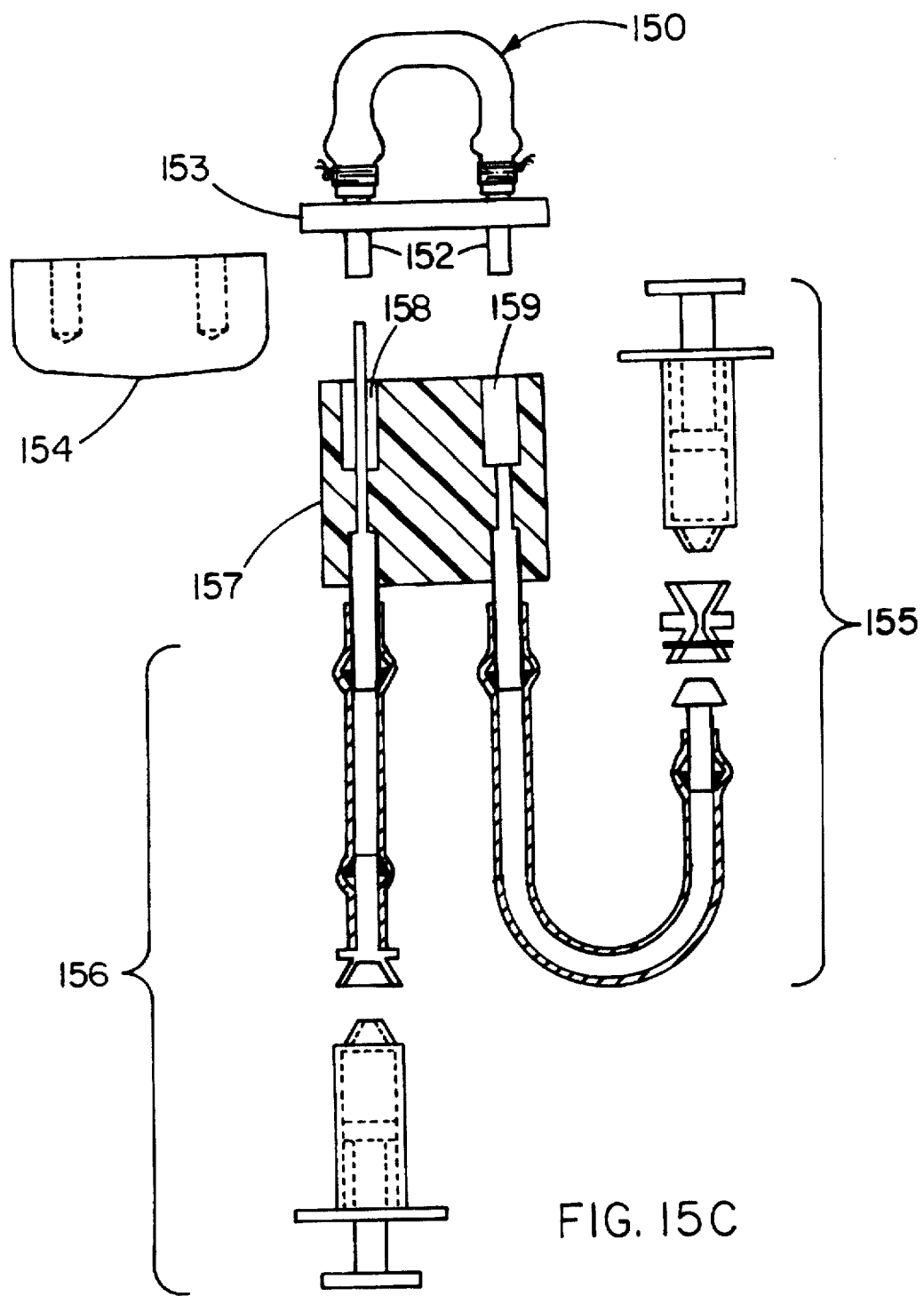
FIG. 15C illustrates a group of assemblies used to place a generally cylindrical therapeutical device in a tubular apparatus of the present invention. The assemblies illustrated in FIG. 15C include an apparatus of the present invention (150) having access means (152), holding means (153), and sealing means (154).

The preferred method of placing, retrieving, and replacing a therapeutical device in a tubular apparatus of the present invention longer than a few centimeters having access means at both ends of the tube is by flushing the therapeutical device in and out of the apparatus with a fluid stream. The method is described using a tubular apparatus of Example 1 having access means at both ends of the tube. The apparatus is also illustrated in FIGS. 14 and 15C. Though not described in Example 1 or shown in FIGS. 14 and 15C, the apparatus of this example has a HYPAN® Structural Hydrogel stent positioned within the entire length of the tube.

In preparation for this experiment, the apparatus was implanted subcutaneously in a greyhound dog and allowed to heal for two weeks. A resilient core of HYPAN® Structural Hydrogel having a generally cylindrical shape was used to simulate a therapeutical device in the method. Construction of the core is described in Example 5, above.

Following a two week healing period, an incision was made in the skin of the experimental animal above the location of the access means to expose the access means. Once the access means was exposed, the sealing means, caps, were removed from the access means. The HYPAN® Structural Hydrogel stents were removed from the ends of the apparatus by forcing saline through the apparatus with a 20 cc syringe causing the stent to squirt out the opposite end of the tube.

The assemblies illustrated in FIG. 15C include an apparatus of the present invention (150) having access means (152), holding means (153), and sealing means (154). FIG. 15C also includes an illustration of two fluid stream means (155 and 156) and a connector (157), having a cavity with a pin (158) on one side (hereinafter the "pin-side") and a cavity (159) on the other side of the connector (157) without a pin (hereinafter the "non-pin-side"), that was adapted to mate with the access means (152) of the apparatus (150) to facilitate placement, retrieval, or replacement of the inert core in the apparatus.

To place the inert core in an apparatus of the type illustrated in FIG. 15C, fluid stream means (155) was filled with an essentially isotonic saline solution. The end of the silicone tube of the fluid stream means attached to the non-pin-side (159) of connector (157) was disconnected from the connector. The inert hydrogel core was placed in the open end of the silicone tube. The open end of the silicone tube was reattached to connector (157) on the non-pin-side (159) of the connector. Fluid stream means (156) was attached to the pin-side (158) of connector (157).

A fluid stream of saline was established with the syringe component of fluid stream means (155) through the silicone tubing entraining the inert hydrogel core in the fluid stream and carrying the core into the luminal space of the tubular apparatus (150). The inert core is prevented from continuing through and out the opposite end of the apparatus by retaining pin (158) in connector (157). Once the inert core was placed in the apparatus, the fluid stream was discontinued. The connector (157) was removed from the access means of the apparatus (152) and replaced with the sealing means (154). The sealed access means was tucked back under the skin and the incision closed.

To remove the inert hydrogel core in the implanted apparatus, the sealed access means were surgically exposed, the sealing means (154) removed, and connector (157), with fluid stream means (155 and 156) attached to the access means of the apparatus (152). A fluid stream was established through the apparatus (150) with fluid stream means (156) around the inert hydrogel core, entraining the core in the fluid stream and moving it out of the apparatus into fluid stream means (155).

To replace another inert hydrogel core in the implanted apparatus, first the silicone tube of fluid stream means (155) was disconnected from the non-pin-side (159) of connector (157) and the initial inert hydrogel core removed from fluid stream means (155). A second inert core was placed in the silicone tube of fluid stream means (155) and the open end of the tube reattached to the non-pin-side (159) of connector (157). The remaining steps are listed above and repeated accordingly.

What is claimed is:

1. A method of loading and reloading a therapeutical device in a vascularized containment apparatus which comprises:

providing an implantable containment apparatus in the form of a chamber comprised of a material having an exterior surface, an interior surface defining a luminal space, and at least one access means through which at least one therapeutical device is insertable into the luminal space of the chamber, wherein the material is impervious to cellular ingrowth across the interior surface of the chamber, wherein therapeutic substances can diffuse across the thickness of the chamber between a therapeutical device contained therein and tissues of a recipient, wherein the therapeutical device is removable from the chamber through the access means of the chamber;

implanting the implantable containment apparatus in a recipient;

allowing cells from the recipient to ingrow the material;

opening the access means of the implantable containment apparatus to access the luminal space of the chamber;

placing a therapeutical device in the luminal space of the chamber through the access means;

closing the access means of the implantable containment apparatus to contain the therapeutical device within the luminal space of the apparatus;

removing the therapeutical device from the luminal space of the implantable containment apparatus through the access means; and reloading the containment apparatus with a therapeutical device through the access means as desired.

2. The method of claim 1 wherein the material comprises porous expanded polytetrafluoroethylene.

3. The method of claim 2 wherein the porous expanded polytetrafluoroethylene is in the form of a laminate.

4. The method of claim 3 wherein the laminate comprises at least two layers of porous expanded polytetrafluoroethylene and wherein at least one layer of porous expanded polytetrafluoroethylene is impervious to cellular ingrowth.

5. The method of claim 1 wherein the material is rendered impervious to cellular ingrowth with a hydrogel material.

6. The method of claim 1 wherein the therapeutical device is a cell encapsulation device.

7. The method of claim 1 wherein the therapeutical device is a drug delivery device.

8. The method of claim 1 wherein the therapeutical device is a gene therapy device.

9. The method of claim 1 wherein the luminal space of the containment apparatus is held open with a stent.

10. The method of claim 1 wherein the cells from the recipient comprise vascular endothelial cells in the form of capillaries.

11. A method of loading and reloading a therapeutical device in a vascularized implantable containment apparatus which comprises:

providing an implantable containment apparatus in the form of a chamber comprised of a material having an exterior surface, an interior surface defining a luminal space, and at least one access means through which at least one therapeutical device is insertable into the luminal space of the chamber, wherein the material is impervious to cellular ingrowth across the interior surface of the chamber, wherein therapeutic substances can diffuse across the thickness of the chamber between a therapeutical device contained therein and tissues of a recipient, wherein the therapeutical device is removable from the chamber through the access means of the chamber;

implanting the implantable containment apparatus in a recipient;

inducing cells from a recipient to ingrow the material;

opening the access means of the implantable containment apparatus to access the luminal space of the tube; and placing a therapeutical device in the luminal space of the chamber through the access means;

removing the therapeutical device from the luminal space of the implantable containment apparatus through the access means; and reloading the containment apparatus with a therapeutical device through the access means as desired.

12. The method of claim 11 wherein the material comprises porous expanded polytetrafluoroethylene.

13. The method of claim 12 wherein the porous expanded polytetrafluoroethylene is in the form of a laminate.

14. The method of claim 13 wherein the laminate comprises at least two layers of porous expanded polytetrafluoroethylene and wherein at least one layer of porous expanded polytetrafluoroethylene is impervious to cellular ingrowth.

15. The method of claim 11 wherein the material is rendered impervious to cellular ingrowth with a hydrogel material.

16. The method of claim 11 wherein the therapeutical device is a cell encapsulation device.

17. The method of claim 11 wherein the therapeutical device is a drug delivery device.

18. The method of claim 11 wherein the therapeutical device is a gene therapy device.

19. The method of claim 11 wherein cells from a recipient are induced to ingrow the material with a biological factor.

20. The method of claim 19 wherein the biological factor is selected from the group consisting of protein cytokines, peptide cytokines, peptides with the amino acid sequence gly-his-lys or their palindromes, polysaccharides, including heparin, angiogenesis stimulating lipids, including oleic acid, and metals, including copper.

21. The method of claim 11 wherein cells from the recipient are induced to ingrow the material under local conditions of hypoxia.

22. The method of claim 11 wherein the luminal space of the containment apparatus is held open with a stent.

23. The method of claim 11 wherein the cells from the recipient comprise vascular endothelial cells in the form of capillaries.

* * * * *